(12) United States Patent
Thess et al.

(10) Patent No.: US 8,148,976 B2
(45) Date of Patent: Apr. 3, 2012

(54) METHOD AND ARRANGEMENT FOR THE CONTACTLESS INSPECTION OF MOVING ELECTRICALLY CONDUCTIVE SUBSTANCES

(75) Inventors: André Thess, Dresden (DE); Yuri Kolesnikov, Riga (LV); Christian Karcher, Ilmenau (DE)

(73) Assignee: Technische Universitat Ilmenau, Ilmenau (DE)

( * ) Notice: Subject to any disclaimer, the term of this patent is extended or adjusted under 35 U.S.C. 154(b) by 1043 days.

(21) Appl. No.: 12/067,794

(22) PCT Filed: Sep. 21, 2006

(86) PCT No.: PCT/EP2006/066605
§ 371 (c)(1),
(2), (4) Date: Mar. 21, 2008

(87) PCT Pub. No.: WO2007/033982
PCT Pub. Date: Mar. 29, 2007

(65) Prior Publication Data
US 2008/0252287 A1    Oct. 16, 2008

(51) Int. Cl.
*G01N 27/72* (2006.01)
*G01R 33/12* (2006.01)
(52) U.S. Cl. ........ 324/228; 324/164; 324/258; 324/269; 324/259; 324/257; 324/232; 324/226; 324/235; 324/236; 324/239; 324/260; 324/261; 324/262
(58) Field of Classification Search ................. 324/228, 324/164, 258, 269, 259, 257, 232, 226, 235, 324/236, 239, 260–262
See application file for complete search history.

(56) References Cited

U.S. PATENT DOCUMENTS
1,793,970 A * 2/1931 Simon et al. ................. 324/71.1
3,023,902 A * 3/1962 Harvengt ................... 209/172.5
(Continued)

FOREIGN PATENT DOCUMENTS
DE        3347190 A1    7/1985
(Continued)

OTHER PUBLICATIONS
A. Thess et al., "Lorentz Foce Velocimetry," Physical Review Letters, Vol. 96 (2006), pp. 164501-1-164501-4.
(Continued)

*Primary Examiner* — Huy Q Phan
*Assistant Examiner* — Lamarr Brown
(74) *Attorney, Agent, or Firm* — Mark D. Wieczorek; Mayer & Williams P.C.

(57) ABSTRACT

The invention relates to a method and arrangement for the contactless determination of conductivity-influencing properties and their spatial distribution over the entire cross section of an electrically conductive substance moving in a primary magnetic field (B). The substance may be a liquid or a solid. A simultaneous measurement of a number of mechanical state parameters of the magnetic system is performed (three-dimensional components of the force and the torque), said parameters being variable by the effect of a secondary field on the magnetic system, the secondary field being produced on the basis of eddy currents induced in the substance by the primary field (B). To determine the spatial distribution of the property that is sought, the primary field is changed in intensity or form a number of times and a measurement of the state parameters is carried out for each change. The determination of the properties sought or their distribution takes place by solving an inverse problem using the method of least squares.

21 Claims, 6 Drawing Sheets

U.S. PATENT DOCUMENTS

| | | | | |
|---|---|---|---|---|
| 3,258,685 | A * | 6/1966 | Horton | 324/204 |
| 3,579,099 | A * | 5/1971 | Kanbayashi | 324/235 |
| 3,609,526 | A * | 9/1971 | Chaberski | 324/226 |
| 3,850,028 | A * | 11/1974 | Thompson et al. | 73/643 |
| 4,471,658 | A * | 9/1984 | Morimoto | 73/643 |
| 4,713,347 | A * | 12/1987 | Mitchell et al. | 436/501 |
| 5,432,444 | A * | 7/1995 | Yasohama et al. | 324/240 |
| 5,793,199 | A * | 8/1998 | Kasahara et al. | 324/204 |
| 6,400,146 | B1 * | 6/2002 | Roy | 324/242 |
| 6,479,991 | B1 * | 11/2002 | Korenaga | 324/226 |
| 6,538,433 | B1 | 3/2003 | Cervantes et al. | |
| 7,426,867 | B2 * | 9/2008 | Koch et al. | 73/627 |
| 2003/0109782 | A1 * | 6/2003 | Su et al. | 600/421 |
| 2005/0122099 | A1 | 6/2005 | Imamoto et al. | |
| 2005/0140365 | A1 * | 6/2005 | Obama et al. | 324/228 |
| 2006/0211938 | A1 * | 9/2006 | Gleich et al. | 600/409 |
| 2007/0052413 | A1 * | 3/2007 | Zimmermann | 324/262 |
| 2007/0155024 | A1 * | 7/2007 | Miethe et al. | 436/524 |
| 2007/0222438 | A1 * | 9/2007 | Reeves | 324/240 |

FOREIGN PATENT DOCUMENTS

| | | |
|---|---|---|
| DE | 4316344 A1 | 11/1994 |
| DE | 19922311 A1 | 11/2000 |
| DE | 10026052 A1 | 12/2001 |
| DE | 102007038635 B3 * | 12/2008 |
| GB | 2312861 A | 12/1997 |
| JP | 57199917 A | 12/1982 |
| JP | 07181195 A | 7/1995 |
| WO | WO0058695 A1 | 10/2000 |

OTHER PUBLICATIONS

J. Baumgartl et al., "The use of magnetohydrodynamic effects to investigate fluid flow in electrically conducting melts," Phys. Fluids, Vol. A5, No. 12 (1993), pp. 3280-3289.

* cited by examiner

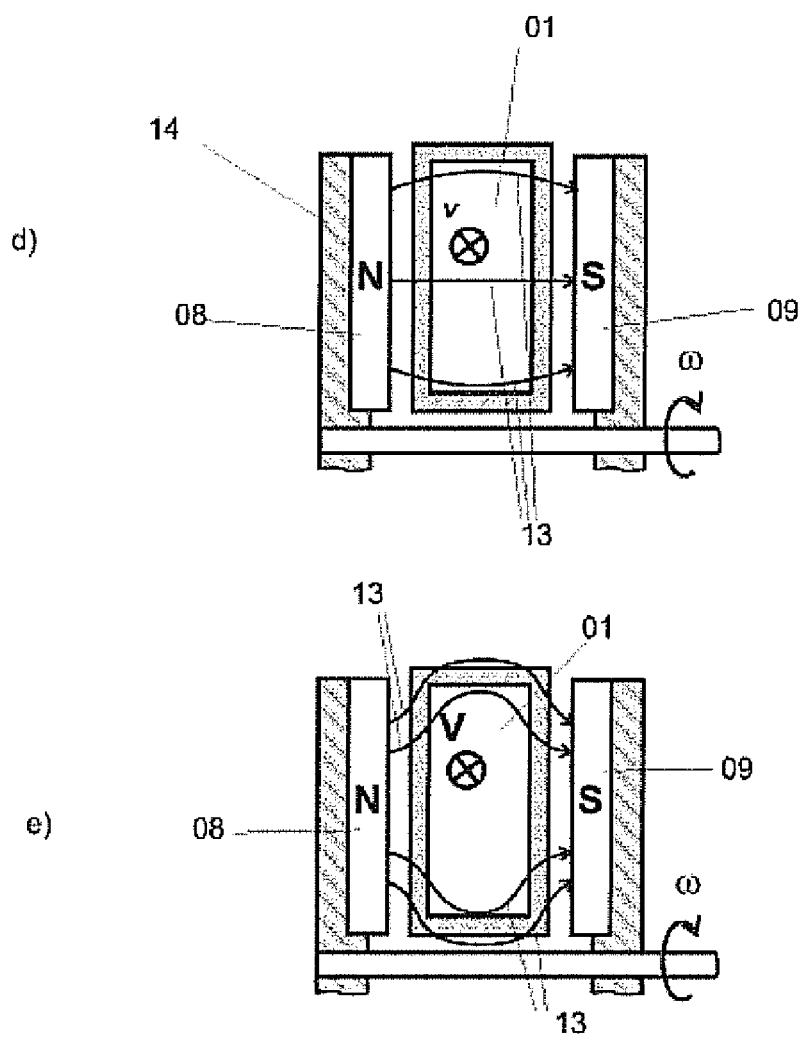
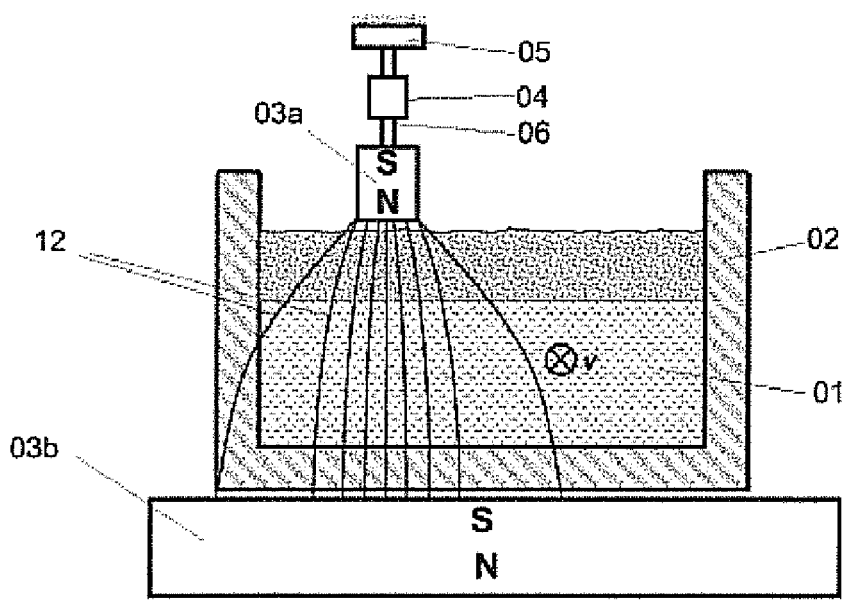
Fig. 4
Fig. 5

METHOD AND ARRANGEMENT FOR THE CONTACTLESS INSPECTION OF MOVING ELECTRICALLY CONDUCTIVE SUBSTANCES

FIELD OF THE INVENTION

The invention concerns a method and arrangement for the contactless determination of properties of electrically conductive moving substances, which can be solid or liquid. In the preferred case of the investigation of liquid substances, these are viewed as a moving substance during flow through a pipe, channel, or similar guiding device. The invention also concerns a method and arrangement for the contactless determination of the spatial distribution of the properties of such substances, such as the flow velocity and electrical conductivity of the substance. The invention can be used in particular for measuring flow and flow volume in metallurgy, but it is also suitable for tasks in nondestructive materials inspection. The arrangement according to the invention shall also be called hereafter a Lorentz force anemometer.

BACKGROUND OF THE INVENTION

The precise measurement of flow velocities, flow volumes, and other properties which affect the electrical conductivity is of great importance, for example, for metallurgical processes, for the growing of semiconductor monocrystals, and for the production of glass. These substances are hot and corrosive during the melt process, so that contactless electromagnetic methods are especially suited for such measuring chores.

Contactless electromagnetic flow measurement methods are known from the publications DE 33 47 190 A1, DE 43 16 344 A1, DE 199 22 311 C2, DE 100 26 052 B4 and the publication "The use of magnetohydrodynamic effects to investigate fluid flow in electrically conducting melts" (J. Baumgartl, A. Hubert, G. Müller, Physics of Fluids, Vol. A 5, Series 1993, pages 3280-3289), in which a magnetic field (the so-called primary field) is coupled into the substance and the magnetic field disturbance induced by eddy currents (the so-called secondary field) serves as a measure of the flow velocity. These methods can be used to determine both mean flow velocities and spatial distributions of the flow velocity, in the latter case making use of the method of least squares of the error to determine the flow distribution.

However, these already known measurement methods have three serious drawbacks. First, due to their limited sensitivity, they do not allow measuring flow velocities in very slowly flowing or very weak electrically conductive substances, such as glass melts. Second, the measurement accuracy of the systems is greatly limited in an electromagnetically perturbed environment, since the magnetic field sensors will be affected by even the slightest parasitic fluctuations of the magnetic field, due to their small spatial dimension. Third, the measurement sensitivity of the method, being characterized by the ratio between secondary field and primary field, cannot be increased by heightening the primary field.

The mentioned drawbacks are only partly remedied by the methods as described in the publications JP 571 999 17 A, U.S. Pat. No. 6,538,433 B1 and JP 071 811 95 A. These are characterized in that, rather than make a direct measurement of the secondary field, one performs a measurement of the force exerted by the secondary field on the system producing the magnetic field. Despite their advantages over the first mentioned methods, the force-measuring systems are of little or no use for a number of important special problems, including flow measurement.

In the layout portrayed in JP 571 999 17 A, the primary magnetic field is generated by coils through which currents flow, entirely surrounding the tubular flow being measured. Such a system is very heavy, it requires an elaborate current supply, and can only be transported to a different place of use after costly disassembly of the measurement system.

The systems presented in the documents U.S. Pat. No. 6,538,433 B1 and JP 071 811 95 A involve local sensors, which can only measure the flow velocity in their immediate surroundings. These local sensors are not suited to determining the mass flow or the volume flow, because the magnetic field generated by them only penetrates part of the cross section through which the conductive substance is flowing. Furthermore, the measurement sensitivity of the local sensors declines with the third power (or even the fourth in the case of greater distances) of the distance from the conductive substance and is therefore not adequate for many application instances.

SUMMARY OF THE INVENTION

Thus, the basic problem of the present invention is to furnish a method and arrangement for the contactless measurement of attributes influencing the electrical conductivity, such as flow velocity and volume flow for electrically conducting substances, which on the one hand allow very high measurement precision and sensitivity. Furthermore, it should be easy to implement such a method. The corresponding arrangement should be economical in construction and easily convertible. Furthermore, it should be possible to determine the spatial distribution of the various properties, such as flow velocity and conductivity in the substance, and also to determine the contour of the gutter (or the like) where the flow is occurring.

The present invention should furthermore enable an identification of inhomogeneities of the electrical conductivity that are localized in time and space, such as slag particles in a melt or cracks in a moving metallic component.

The entirety of the measurement problems whose goal is in particular to discover the distributions of flow velocities and electrical conductivity in an electrically conductive substance shall be summarized hereafter by the term, inspection.

The mentioned problems are solved, according to the invention, by the features of the independent claims 1 and 13, while the subclaims reveal advantageous modifications of the invention.

The advantages of the invention are to be seen, in particular, in that the system producing the magnetic field is designed to be so flexible that it can at any time be taken down, rearranged, and used for other measurement problems. As compared to the existing stationary sensors which only scan the substance locally, an improved utilization of the magnetic field lines in the invention, along with minimal use of material to generate the magnetic field, is an advantage.

If an electrically conductive substance is moving relative to a magnetic field, the primary magnetic field, the eddy currents induced in the substance will cause a disturbance of the magnetic field, the secondary magnetic field. The structure of the secondary magnetic field depends on the distribution of the primary magnetic field, as well as the distributions of the flow velocity (i.e., the velocity with which the substance is moving, if only partially, in the primary field) and the electrical conductance of the substance.

The secondary magnetic field exerts forces and torques on a magnetic system producing the primary field, hereinafter known as Lorentz forces, regardless of the physical details of their creation.

Now, because of these Lorentz forces on the magnetic system, according to the invention, it is possible to obtain information as to the flow velocity and the electrical conductance of the substance.

Due to the central role of the Lorentz force, the proposed arrangement of the invention shall be called a Lorentz force anemometer.

The Lorentz force anemometer comprises a magnetic system with at least two magnetic poles (NORTH and SOUTH) to create the primary field. The poles are preferably arranged at basically opposite sides of the cross section of a substance being inspected. The substance is thus arranged in the air gap of the magnetic system. This arrangement ensures that the primary field or the lines of force running between NORTH and SOUTH in the air gap pass through the entire cross section of the substance and thus create the precondition for a complete determination of the spatial distribution of flow velocity and electrical conductance.

In an especially advantageous embodiment, the poles of the magnetic system can be removed from the Lorentz force anemometer. This feature enables a flexible use of the arrangement. On the one hand, the Lorentz force anemometer can easily be mounted on various layouts being measured, and on the other hand this enables an easy packaging of the Lorentz force anemometer for different conditions of use.

An actuator system coupled to the magnetic system allows a specific setting of at least one parameter of the primary magnetic field.

The variation of at least one parameter of the primary magnetic field, hereinafter known as the actuating variable, serves the purpose of concentrating the lines of the magnetic field on certain partial regions of the substance being inspected so as to scan the distribution of flow velocity and electrical conductance.

The primary magnetic field produced by the magnetic system can be configured, according to the invention, as either a direct field or an alternating field.

In the configuration of the invention, the magnetic system can consist of permanent magnets, of normally conducting or superconducting coils, or of a combination of these elements. Moreover, the magnetic system can contain components of magnetically conducting material as well as ferrofluids, making possible a specific shaping of the primary magnetic field.

The actuating variable can be, for example, the distance between the magnetic system and the substance being inspected, the speed of rotation of the magnetic system, the strength of the magnetic field or the aperture angle of an elliptical cylinder. Elliptical cylinders are special arrangements of permanent magnets that are characterized by an especially high intensity and homogeneity of tie magnetic field prevailing in them. A more detailed explanation will be given in the description of the figures.

The magnetic system is characterized by so-called state parameters, at least one of which varies under the influence of the Lorentz forces with the actuating variable held constant. That is, under the influence of the Lorentz forces, various forces and torques act on the magnetic system, bringing about a movement and/or deformation of the magnetic system, which can then be measured.

One state parameter can be, e.g., a component of a three-dimensional displacement vector, which describes the translation of the magnetic system as a whole under the influence of the Lorentz force.

Another state parameter can be a component of a three-dimensional rotation vector, which describes the rotation of the magnetic system as a whole by the torques produced by the Lorentz forces.

Moreover, the state parameters can be internal stresses, as well as elastic deformations of the magnetic system.

The inspection of the electrically conductive substance occurs by measuring and evaluating one or more state parameters. In the method of the invention, one distinguishes between a monitoring mode and an exploratory mode.

In the monitoring mode, the actuating variables are held constant and at least one, preferably several, of the state parameters are measured as a function of time. This makes it possible to determine individual properties of the substance being inspected, such as flow rate, mean electrical conductance or level of filling in a flow channel, pipe, gutter, or the like, as a function of time. The monitoring mode is the basic function of the Lorentz force anemometer.

The exploratory mode is an expansion of the invented method, making it possible not only to determine individual properties, but also to fully ascertain a spatial distribution of the properties, such as flow velocity and electrical conductance in a substance being inspected. In the exploratory mode, preferably with the help of an actuator system, at least one actuating variable is varied in a defined way and at the same time at least one state parameter is measured.

If one knows a cross sectional shape of the substance being inspected, one can calculate the relation between measured and sought variables in customary fashion, known to the practitioner, starting from the fundamental equation of magnetohydrodynamics.

In practice, the shape of the actual flow cross section is often not known with precision, since it changes over the course of time due to erosion processes or build-up of slag in the pipe. Therefore, a switching from the monitoring mode to the exploratory mode takes place in the Lorentz force anemometer of the invention.

It is also conceivable to continually measure at least two state parameters in the monitoring mode and infer changes in certain properties by solving an inverse problem.

By solving the inverse problem, from the measured state parameters one determines field variables, such as a velocity profile of a flow, a contour of a flow gutter, or the position and shape of a crack in a solid.

The inverse problem is solved by the method of least error squares. The function to be minimized is the mean square deviation of the state parameter, as calculated by the assumed distribution of the properties such as electrical conductance and flow velocity, from the respective measured state parameters.

BFIEF DESCRIPTION OF THE DRAWING

Further details and benefits of the invention will be seen from the following sample embodiments, explained with the help of the figures, in which FIG. 1 shows a first embodiment of a Lorentz force anemometer with a static and homogeneous primary field;

FIG. 5 shows a fifth embodiment of the Lorentz force anemometer with a static primary field and a two-part magnetic system;

DETAILED DESCRIPTION OF THE INVENTION

Figure 1:
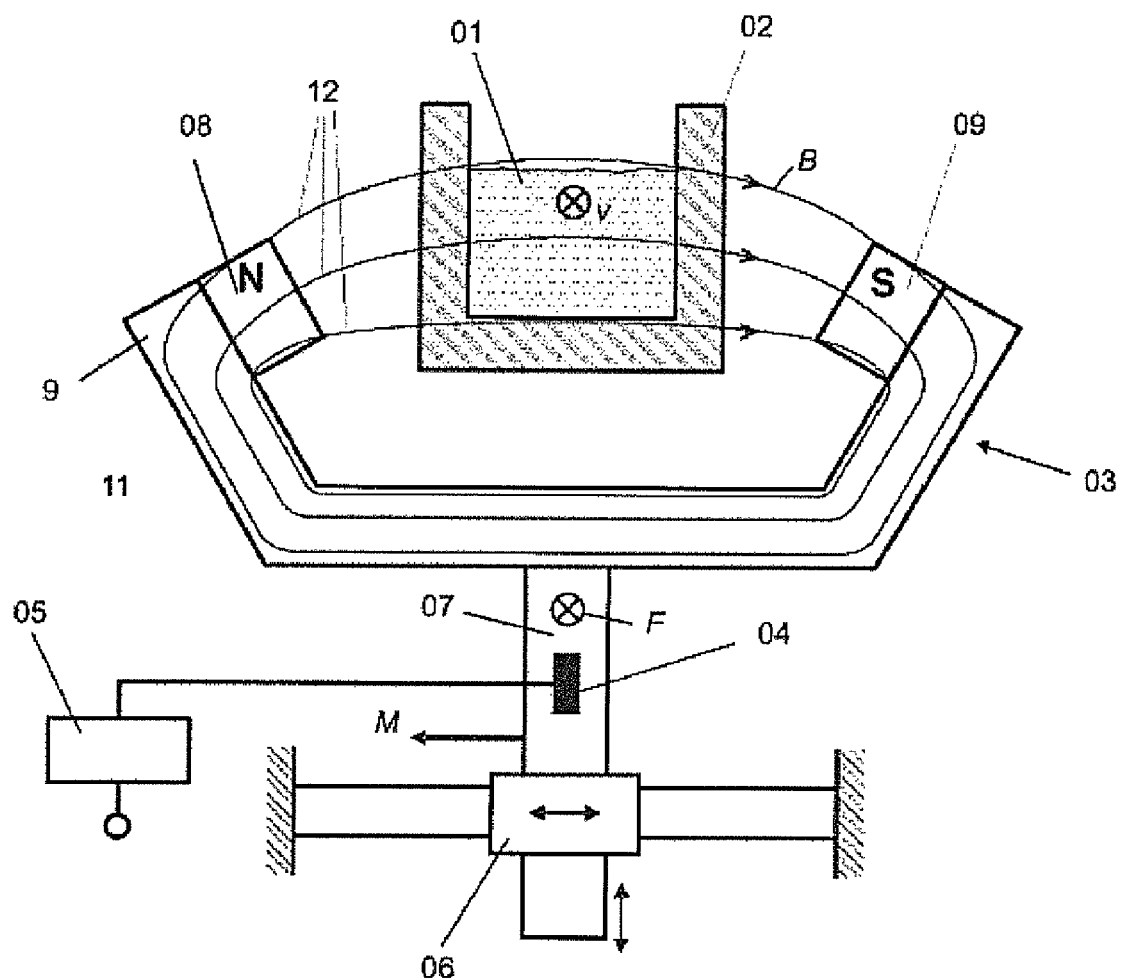

FIG. 1 shows a first preferred embodiment of the invented Lorentz force anemometer for contactless inspection of a substance 01, which is flowing in a channel 02 (hereinafter also called a gutter). The flow velocity of the substance 01 is indicated by the vector v. The Lorentz force anemometer comprises a magnetic system 03, a measurement system 04, an evaluation unit 05 and an actuator system 06. Magnetic system 03, evaluation unit 05 and actuator system 06 are arranged in a common holder 07.

The magnetic system 03 comprises at least two permanent magnets 08, 09, arranged opposite each other, outside of the gutter 02, and a yoke 11 of a magnetically conducting material. It serves to generate a primary field B, which is represented by its field lines 12.

Integrated in the holder 07 is the measurement system 04, preferably containing several strain gage strips, which measures the state parameters of the substance 01. The state parameters are preferably components of the force F and the torque M acting on the magnetic system 03 and the holder 07 due to the Lorentz forces.

The mode of operation of such a measurement system 04 corresponds to that of wind tunnel scale, which already finds application in aerodynamics, for example. The measurement system 04 can thus be designed and built in a manner familiar to the practitioner.

In the monitoring mode, the magnetic system 03 is arranged stationary to the gutter 02. Then from the preferably six measured state parameters, one calculates in the evaluation unit 05 at most six properties of the substance 01 being inspected, such as flow rate, level of filling, flow cross section, shear rate, inclination, and mean electrical conductance, as functions of time.

Of course, it is within the scope of the invention, if need be, to measure and evaluate a subset of the six state parameters, such as only the force acting in the principal direction of flow.

In the embodiment depicted, the magnetic system 03 can be positioned at different places by the actuator system 06, preferably outfitted with step motors. The exploratory mode can be implemented in this way. In the exploratory mode, the magnetic system 03 is positioned at various different points one after the other and/or the primary field is varied in a defined manner. At each of these points or upon each such variation, a measurement of the state parameters (six force and torque components) takes place.

By solving an inverse problem, one calculates in the evaluation unit 05 both the profile of the desired property, preferably the flow velocity, and the profile of the electrical conductance of the substance 01. From the latter, one gets the shape of the gutter 02 and the shape of the free surface of the substance 01.

The invented Lorentz force anemometer with exploratory mode thus allows one to carry out a flow measurement even when the flow geometry is not precisely known. Furthermore, the exploratory mode makes it unnecessary to have a precise, predetermined positioning of the Lorentz force anemometer with respect to the substance 01 being inspected and thus increases the flexibility of the system and makes it unnecessary to use costly positioning systems.

Instead of using strain gage strips in the measurement system 04, it may be advantageous to perform the force and torque measurement by means of optical methods or by means of a compensation method.

It should be pointed out once again, for clarity, that the substance can also be a solid component which is moved in the primary field. The component can be guided in traditional manner by bearings or the like, which take over the function of the gutter.

Figure 2:
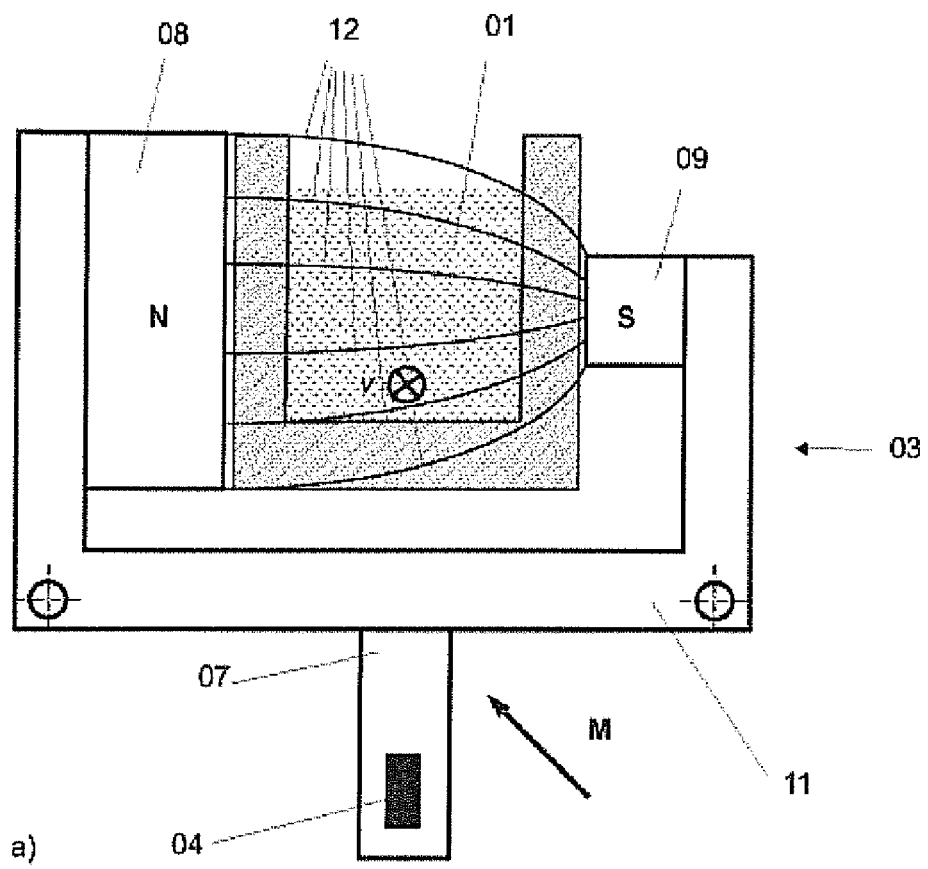
FIG. 2 shows a second embodiment of a Lorentz force anemometer with a magnetic system for generating a static and inhomogeneous primary field.
Figure 2:
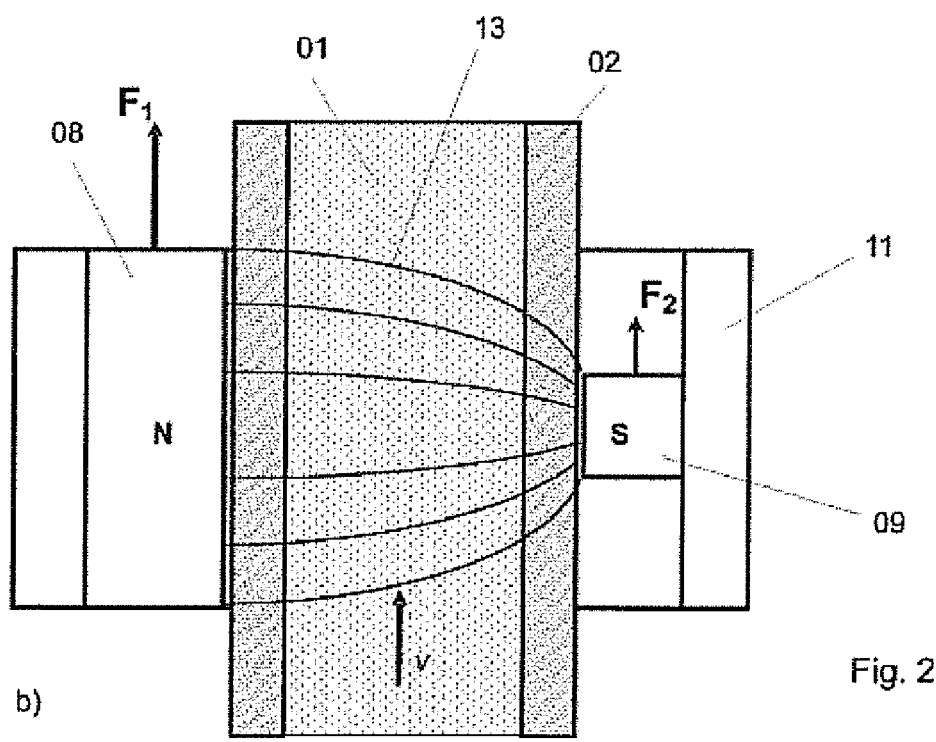

FIG. 2 shows a second embodiment of a Lorentz force anemometer. In this embodiment, the magnetic system 03 is asymmetrical and so the primary field B has an inhomogeneous configuration. The oppositely placed permanent magnets 08, 09 have different sizes and/or different magnetization strengths. The inhomogeneous design of the magnetic field B has the advantage that all components of the force F and the torque M acting on the magnetic system 03 (i.e., all state parameters) are different from zero, thereby achieving maximum information about the substance 01.

This circumstance is illustrated in part a of FIG. 2 by representing the directional vector of the torque M acting on the magnetic system 03. In contrast to this, the vertical force component in the system shown in FIG. 1, for example, is equal to zero because of the left/right symmetry and does not contribute to the information obtained.

Part b of FIG. 2 shows a plan view of the Lorentz force anemometer of the second embodiment. One recognizes the force components F1 and F2 of different magnitude, as well as the velocity vector v of the substance 01.

Figure 3:
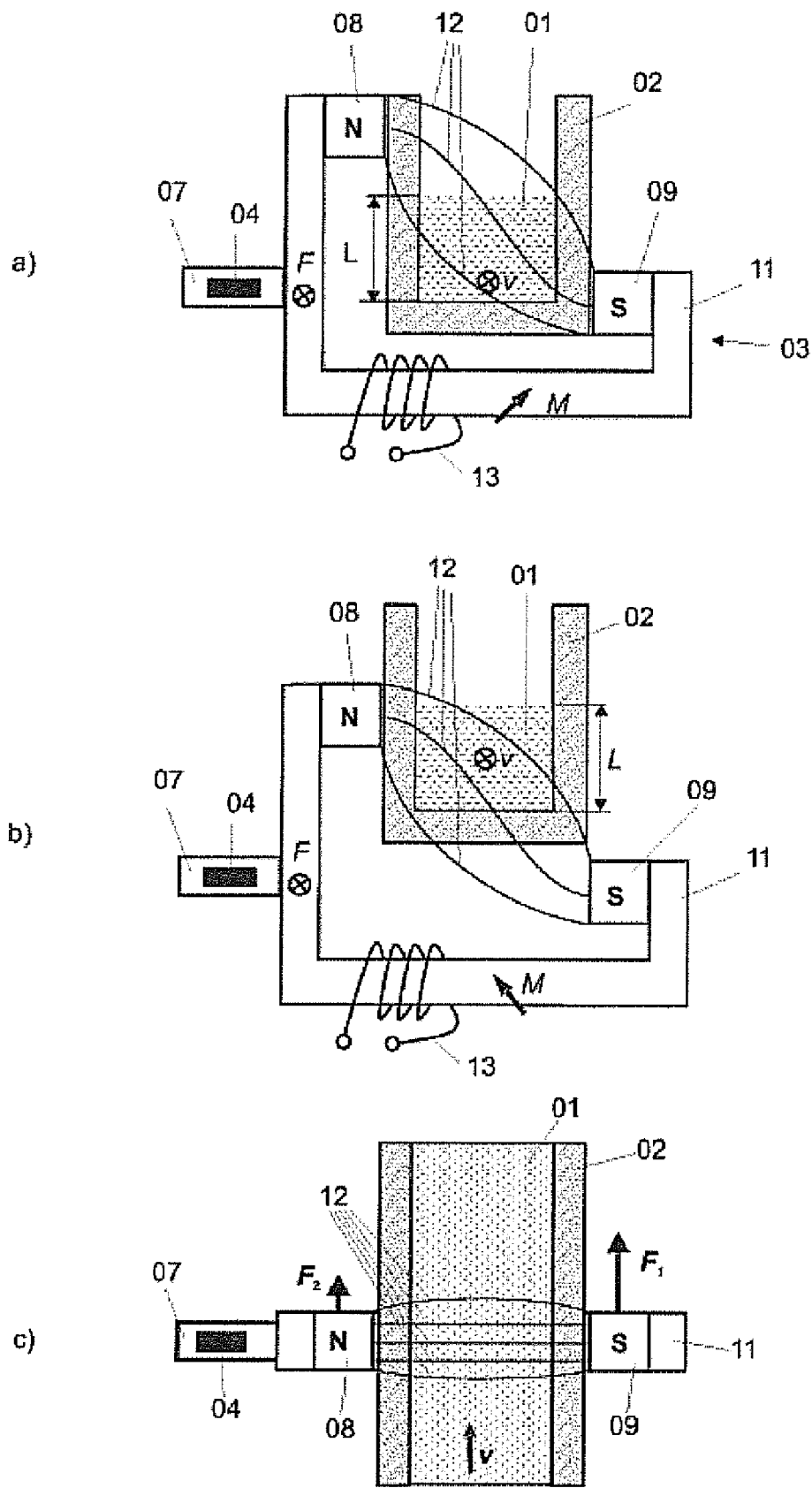
FIG. 3 shows a magnetic system of a third embodiment with a static and inhomogeneous primary field in the exploratory mode.

FIG. 3 shows, in a third embodiment of the invented Lorentz force anemometer, a magnetic system 03 with inhomogeneous primary magnetic field B in exploratory mode. Parts a and b of the figure show different positions of the magnetic system 03 relative to the substance 01, part c shows a plan view of part a. The magnetic system 03 has two poles, consisting of permanent magnets 08, 09, which are arranged with a horizontal offset relative to each other and magnetically joined together by the yoke 11. This produces an inhomogeneous primary field B, which is shown by the field lines 12 drawn. The overall magnetic system 03 can be moved vertically by means of the actuator system 06, not shown. The yoke 11 is at least partly enclosed by a coil 13. The strength of the primary field B created by the permanent magnets 08, 09 and the coil 13 is varied by the size of the current flow in the coil 13.

The magnetic system 03 shown in FIG. 3 has two actuating variables for the exploratory mode, namely, the vertical position L, which can be changed by translation, and the strength of the primary magnetic field B, which can be changed by varying the current strength in the coil 13.

If the magnetic system 03 is in the upper position, shown in part a and c of FIG. 3, a greater Lorentz force F1 will act on the permanent magnet 09 situated at bottom right in part a of the figure than on the permanent magnet 0 situated at top left (force F2). The torque M acting on the overall magnetic system 03 in this case points upper right, as is shown by the vector arrow M in FIG. 3a.

If the magnetic system 03, as shown in FIG. 3b, is in the bottom position, a greater Lorentz force will act on the permanent magnet 08 situated at upper left in this figure than on the permanent magnet 09 situated at bottom right and the direction of the torque M will change accordingly.

In the exploratory mode, the strain gage strips integrated in the measuring system 04 measure the state parameters (force and torque components) acting on the magnetic system 03, and this is performed at a plurality of vertical positions L of the magnetic system 03 and for a plurality of current strengths of the current flowing through the coil 13. If it is also desired to ascertain a distribution of the properties along a given length of the channel or gutter 02, this can be done by an appropriate positioning of the magnetic system at a second or several points of the channel 02.

From the measured state parameters, the evaluation unit (not shown) determines the profile of the flow velocity v and the electrical conductance of the substance 01, once again by solving an inverse problem. Since the electrical conductance has a discontinuity at the boundary between the substance 01 being inspected and the wall of the gutter, one also gets the shape of the gutter 02 in this way.

Figure 4:
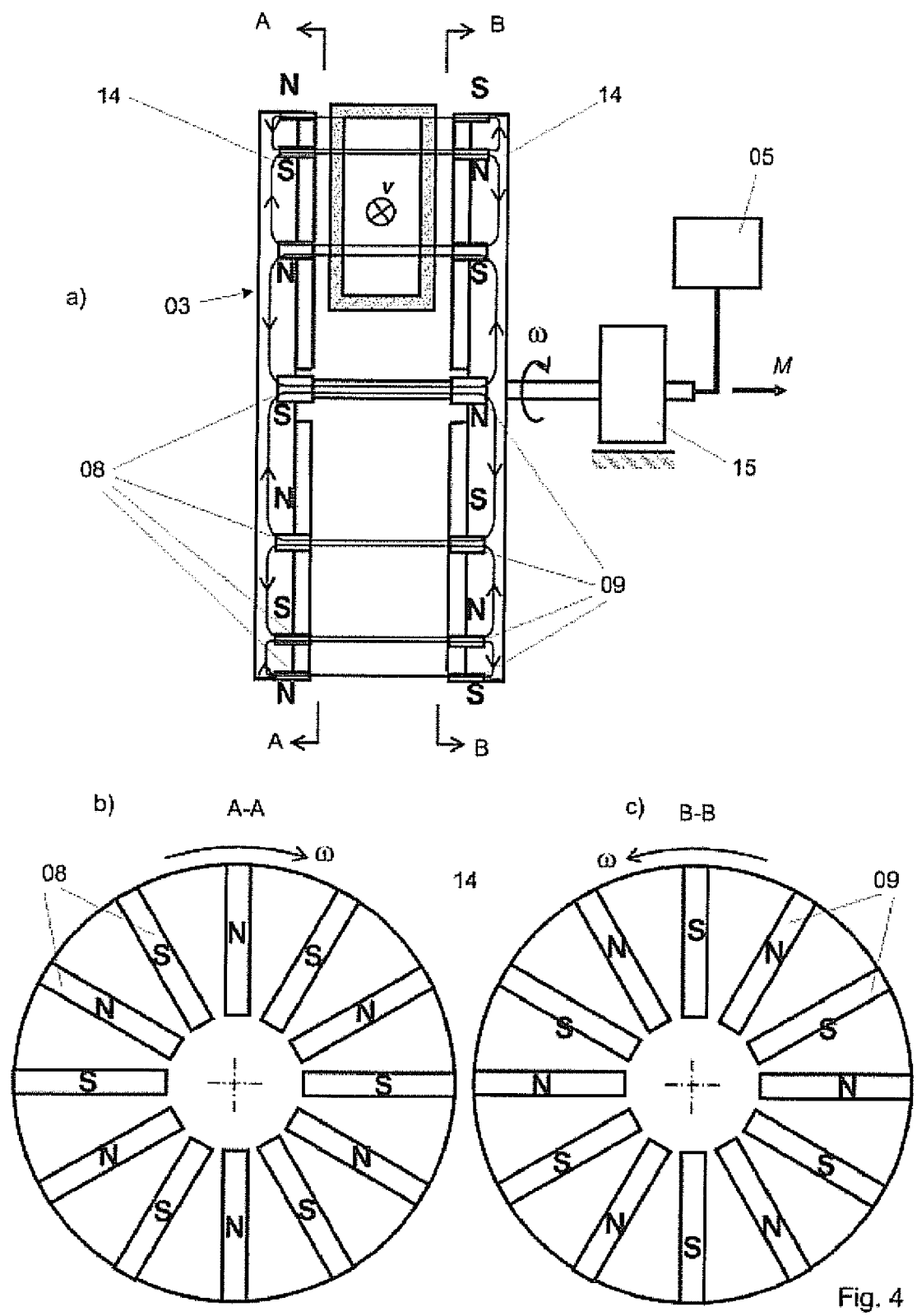
FIG. 4 shows a fourth embodiment of the Lorentz force anemometer with a rotating primary field.

FIG. 4 shows a fourth embodiment of the Lorentz force anemometer with a rotating primary field B. The magnetic system 03 in this case comprises two oppositely placed disks 14 of magnetically conductive material, joined together, which form the yoke, in which a plurality of permanent magnets 08, 09 with alternating polarity are embedded or glued on (FIG. 4b and c).

This disks 14 are arranged opposite each other so that each time one magnetic north pole of a permanent magnet 08 lies opposite a magnetic south pole of a permanent magnet 09.

In the exploratory mode, the magnetic system 03 is placed in rotation by the Lorentz force generated by the moving substance 01 and the rotary speed ω is measured continually by means of a tachometer 15. From the measured speed ω, the evaluation unit 05 calculates the sought property of the substance 01, such as the flow rate.

It also within the scope of the invention to install a motor with integrated torque measuring system, instead of the tachometer 15. In the monitoring mode, then, the motor will rotate with a defined rotary speed. At the same time, the torque produced by it will be measured and from this the sought property of the substance 01, such as the flow rate, will be calculated in the evaluation unit 05.

In the exploratory mode, the speed ω of the magnetic system 03 shown in FIG. 4 constitutes the actuating variable, while the torque M embodies the state parameter. If the speed ω is low, the lines of the magnetic field 12 entirely penetrate the substance being inspected 01 (FIG. 4d).

But if the speed ω is great (FIG. 4e), the lines of the magnetic field 12 are displaced from the substance 01 by virtue of the skin effect and only move through the regions of the substance 01 near the walls. Thus, by varying the speed ω, one can deliberately influence the distribution of the primary field B at the site of the substance being inspected 01.

In the exploratory mode, the measuring system integrated in the motor measures the torque M acting on the magnetic system 03 for a plurality of speeds ω. From this, the evaluation unit 05 calculates the profile of the flow velocity and the electrical conductance of the substance 01, again by solving an inverse problem.

FIG. 5 shows a fifth embodiment of the Lorentz force anemometer. The magnetic system 03 is two-part and comprises an active component 03a and a passive component 03b. The passive component 03b of the magnetic system 03 is arranged stationary beneath the substance being inspected 01, while the active component 03a of the magnetic system 03 is positioned above the substance 01. The substance 01 is covered with a layer of slag.

In the monitoring mode, the active component 03a is also stationary. By measuring or plotting one or more state parameters (force and torque components) acting on the active component 03a of the magnetic system 03 by means of the measurement system 04 as a function of time, the sought property of the substance, such as the flow rate, is calculated in the evaluation unit 05.

In the exploratory mode, the position of the active component 03a relative to the substance 01 and to the passive component 03b is changed in a defined manner by means of the actuator system 06 and at the same time one measures the force and torque components acting on the active component 03a of the magnetic system 03 by means of the measurement system 04. By solving an inverse problem, the profiles of velocity v and electrical conductance of the substance are calculated from this in the evaluation unit 05.

Figure 6:
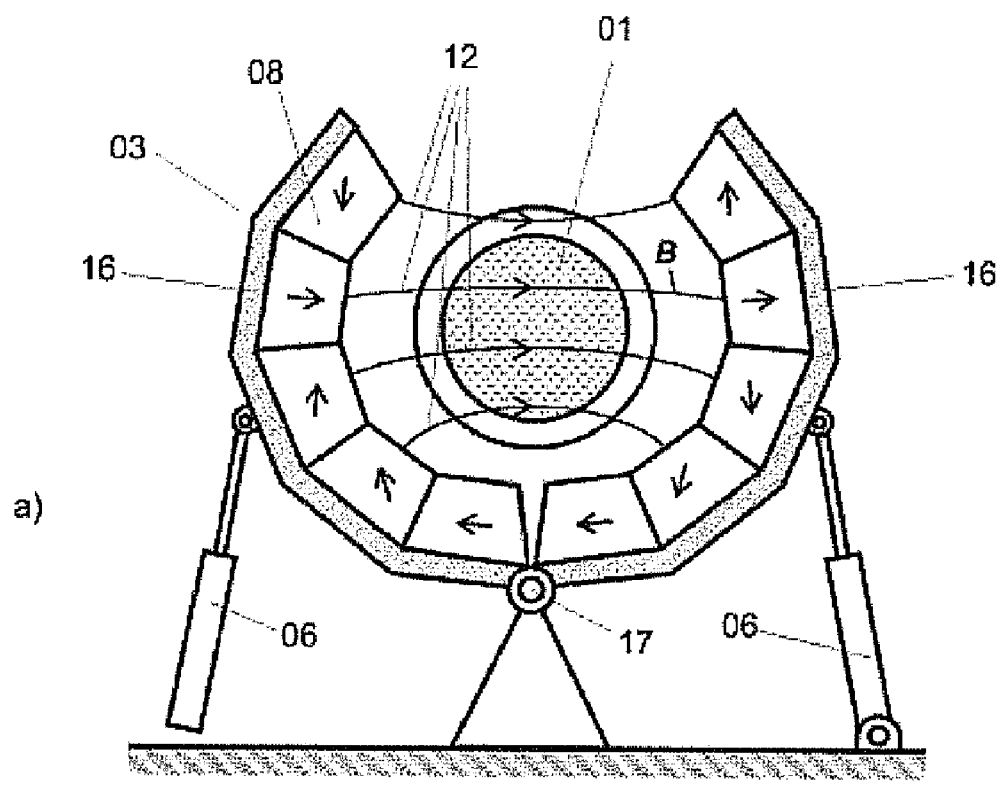
FIG. 6 shows a sixth embodiment of the Lorentz force anemometer with a magnetic system in the form of a fold-out elliptical cylinder.
Figure 6:
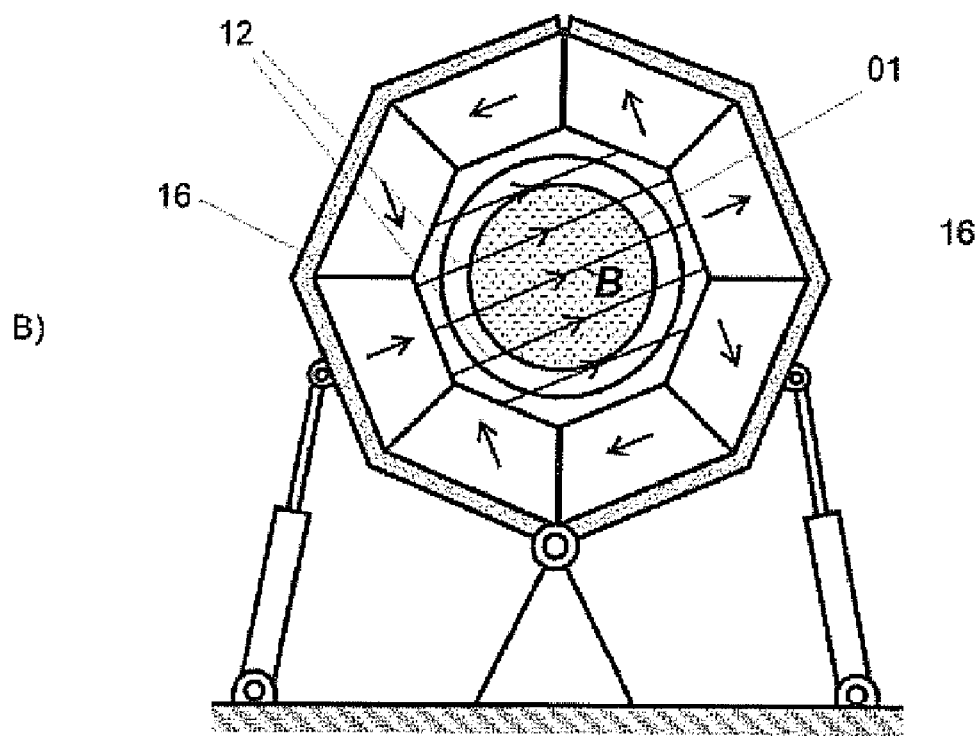

FIG. 6 shows in a sixth embodiment of a Lorentz force anemometer a magnetic system 03, which is designed as a fold-open elliptical cylinder. In this embodiment, the permanent magnets 08, 09 are fastened to a housing consisting of two half shells 16. The half shells 16 are joined together by means of a hinge 17 and can be opened and closed by means of the actuator system 06.

In the open state (FIG. 6a), the magnetic system 03 can be removed and it generates an inhomogeneous magnetic field B in the substance being inspected 1. In the closed state (FIG. 6b), the magnetic field B is homogeneous and possesses a maximum value.

Of course, it also falls within the scope of the invention to vary the aperture angle of the elliptical cylinder continuously in the exploratory mode.

In the monitoring mode, the aperture angle of the elliptical cylinder is held constant and once again the force and/or torque components acting on it are ascertained as state parameters as a function of time by the measurement methods described in the preceding sample embodiments.

In the exploratory mode, the force and torque components acting on the magnetic system 03 are measured for a plurality of aperture angles of the elliptical cylinder and once again used in the evaluation unit (not shown here) to solve an inverse problem and calculate the profile of flow velocity and electrical conductance of the substance being inspected.

LIST OF REFERENCE NUMBERS

01 electrically conductive substance
02 channel/gutter
03 magnetic system
  03a active component of the magnetic system
  03b passive component of the magnetic system
04 measurement system
05 evaluation unit
06 actuator system
07 holder
08 permanent magnet
09 permanent magnet
10 -
11 yoke
12 field lines
13 coil
14 disk
15 tachometer
16 half shell
17 hinge
v flow velocity
B magnetic primary field
F force
M torque
ω rotary speed

The invention claimed is:

1. A method for the contactless determination of properties influencing the conductance of an electrically conductive substance moving in a primary magnetic field (B), comprising the following steps:
coupling a primary magnetic field (B) into a substance being inspected using a magnetic system with at least two poles, wherein lines of force of the primary field (B) running in an air gap between the at least two poles penetrate the substance and run substantially transverse to a direction of movement of the substance;

measuring at least one mechanical state parameter of the magnetic system, the at least one mechanical state parameter changing due to an action of a secondary field on the magnetic system, the secondary field being formed by eddy currents induced in the substance by the primary field (B);

calculating at least one property influencing a conductance of the substance method of least error squares, wherein a function being minimized is a mean square deviation of the at least one state parameter as calculated by an assumed spatial distribution of the at least one property of the substance being inspected from the respective measured state parameters.

2. The method of claim 1, wherein the following steps are additionally carried out to determine the spatial distribution of the properties of the substance which influence the conductance:

changing the shape and/or strength of the primary magnetic field (B) passing through the substance;

measuring the mechanical state parameters of the magnetic system for every change in the primary field (B);

calculating the spatial distribution of the properties influencing the conductance of the substance being inspected across its entire cross section, using the method of least error squares, wherein the function being minimized is the mean square deviation of the state parameters as calculated by the assumed spatial distribution of these properties of the substance being inspected from the respective measured state parameters.

3. The method of claim 2, wherein a determination of the spatial distribution of the properties is also done along a given length of the substance in its axial direction of movement by carrying out the mentioned steps of the method for at least two axially separated points of the substance.

4. The method of claim 1, wherein the primary magnetic field (B) is a direct field or an alternating field.

5. The method of claim 1, wherein the state parameters of the magnetic system are three-dimensional components of the force (F) and/or the torque (M), acting on the magnetic system by virtue of the secondary field caused by eddy currents induced in the substance.

6. The method of claim 5, wherein the state parameters of the magnetic system are determined with a compensation measurement method.

7. The method of claim 1, wherein the state parameters of the magnetic system are determined from mechanical stresses occurring in the magnetic system.

8. The method of claim 2, wherein the shape and/or the strength of the primary magnetic field (B) is changed by a changing of position of the magnetic system relative to the substance being inspected.

9. The method of claim 2, wherein the strength of the primary magnetic field (B) is changed by varying a current flowing through a coil surrounding at least part of the magnetic system.

10. The method of claim 1, wherein the primary magnetic field (B) is inhomogeneous in configuration.

11. The method of claim 1, wherein the substance is an electrically conductive solid and the property being determined is the position and/or form of an inhomogeneity in the solid.

12. The method of claim 1, wherein the properties of a fluid substance are determined, which is moving in a channel or the like, which extends transversely to the lines of force running in the air gap.

13. A Lorentz force anemometer for contactless determination of properties influencing the conductance of a moving electrically conductive substance, comprising:

a magnetic system for generating a primary field (B), including a yoke and at least two magnetic poles, wherein a substance can be moved in an air gap between the poles transverse to a direction of the primary field;

a measurement system to detect at least two mechanical state parameters of the magnetic system, the state parameters characterizing a mechanical action of a secondary field on the magnetic system, wherein the secondary field arises by virtue of eddy currents induced in the substance moving in the primary field; and an evaluation unit to determine at least one property influencing a conductance of the substance from the measured state parameters.

14. The Lorentz force anemometer of claim 13, further comprising an actuator system, which is coupled to the magnetic system in such a way as to allow a changing of position of the magnetic system relative to the substance, thereby achieving a change in the form and/or strength of the primary magnetic field (B) in the cross section of the substance.

15. The Lorentz force anemometer of claim 13, wherein the poles are formed by permanent magnets.

16. The Lorentz force anemometer of claim 15, wherein the permanent magnets are of different strength and/or size, so that an inhomogeneous primary field (B) is formed.

17. The Lorentz force anemometer of claim 13, wherein the poles of the magnetic system are formed by normally conducting or superconducting coils or by a combination of such coils with permanent magnets.

18. The Lorentz force anemometer of claim 13, wherein the poles of the magnetic system are formed by two oppositely arranged disks with permanent magnets arranged on them with alternating polarity, and the disks are joined by a yoke and can be driven centrally.

19. The Lorentz force anemometer of claim 18, wherein the disks rotate with a speed ω which can be adjusted and varied by a drive unit.

20. The Lorentz force anemometer of claim 13, wherein the magnetic system comprises magnetically conductive material and ferrofluids to form the primary magnetic field 21. The Lorentz force anemometer of claim 13, wherein a channel runs in the air gap between the poles, in which a liquid flows as the substance being inspected.

* * * * *